(12) United States Patent
Appel et al.

(10) Patent No.: US 8,454,981 B2
(45) Date of Patent: *Jun. 4, 2013

(54) COSMETIC PREPARATION FOR COLORING THE EYELIDS AND EYEBROWS

(75) Inventors: Tatiana Appel, Oberasbach (DE); Gerhard Lugert, Nürnberg (DE)

(73) Assignee: Faber-Castell AG, Stein (DE)

( * ) Notice: Subject to any disclaimer, the term of this patent is extended or adjusted under 35 U.S.C. 154(b) by 959 days.

This patent is subject to a terminal disclaimer.

(21) Appl. No.: 11/875,983

(22) Filed: Oct. 22, 2007

(65) Prior Publication Data

US 2008/0102047 A1    May 1, 2008

(30) Foreign Application Priority Data

Oct. 20, 2006  (EP) .................................. 06021996

(51) Int. Cl.
  *A61Q 1/10*  (2006.01)
(52) U.S. Cl.
  USPC ......................................................... 424/401
(58) Field of Classification Search
  None
  See application file for complete search history.

(56) References Cited

U.S. PATENT DOCUMENTS

| | | | |
|---|---|---|---|
| 6,726,917 B2 * | 4/2004 | Kanji et al. | 424/401 |
| 6,946,518 B2 * | 9/2005 | De La Poterie | 525/50 |
| 2002/0192170 A1 | 12/2002 | Appel et al. | |
| 2006/0117995 A1 | 6/2006 | Appel et al. | |

FOREIGN PATENT DOCUMENTS

| | | |
|---|---|---|
| DE | 202004018813 U1 | 5/2006 |
| EP | 1247514 A2 | 10/2002 |
| GB | 1193829 A | 6/1970 |
| JP | 61027913 A | 2/1986 |
| JP | 4173718 A | 6/1992 |
| JP | 2002363031 * | 12/2002 |
| JP | 2002363031 A | 12/2002 |
| JP | 2004315459 A | 11/2004 |
| JP | 2006249023 A | 9/2006 |

\* cited by examiner

*Primary Examiner* — Jyothsna Venkat
(74) *Attorney, Agent, or Firm* — Laurence A. Greenberg; Werner H. Stemer; Ralph E. Locher

(57) ABSTRACT

An aqueous cosmetic preparation for coloring the eyelids and eyebrows contains 0.1% by weight to 5% by weight of polyvinyl pyrrolidone; 4% by weight to 25% by weight of an alcohol from the group of ethanol and propanol; 2% by weight to 15% by weight of a dampening agent; 0.1% by weight to 5% by weight of polyoxyethylene glycerin fatty acid ester and/or polyether-modified polysiloxane; and a colorant. The cosmetic preparation has a viscosity of less than 50 mPas (Brookfield, 25° C.).

3 Claims, No Drawings

COSMETIC PREPARATION FOR COLORING THE EYELIDS AND EYEBROWS

CROSS-REFERENCE TO RELATED APPLICATION

This application claims the priority, under 35 U.S.C. §119, of European application EP 06 021 996.1, filed Oct. 20, 2006; the prior application is herewith incorporated by reference in its entirety.

BACKGROUND OF THE INVENTION

Field of the Invention

The invention concerns a cosmetic preparation for coloring the eyelids and eyebrows. In the past, coloring the aforementioned parts of the skin has been accomplished primarily using relatively highly viscous preparations, which are applied using flat brushes or painting brushes, etc. A precise application is difficult to achieve in this manner. Furthermore, it is necessary to remove preparation from a container multiple times in order to provide the desired parts of the skin with an even layer of color. In doing so, the preparation frequently cannot be prevented from dripping off of the applicators. For this reason capillary applicators are widely used today, with which the aforementioned handling problems are largely solved. The problem with capillary applicators is that the preparations must be of relatively low viscosity so that they can be drawn out of their container by the capillary system of an applicator. However, the preparations must also fulfill the requirements for a preparation with the intended purpose, i.e. they should provide the best possible coverage of color, with a degree of permanence that is sufficient for the eye area, and must be easily removable with cleansing. These are properties that are difficult to achieve with low viscosity preparations, because these penetrate easily into the skin due to their low viscosity, which also makes them more difficult to remove with cleansing. Low viscosity preparations also tend to penetrate into creases and pockets in the skin, and to run in them, so that colored areas of the skin with somewhat smooth margins are difficult to create. Instead, a more frayed appearance is created. From a technical point of view, in other words the suitability of a preparation for use with capillary applicators, low viscosity alone is not sufficient. For instance, it must be ensured that the preparation does not dry out during periods of non-use, which would impair the capillary function of an applicator element, such as a sintered tip.

BRIEF SUMMARY OF THE INVENTION

It is accordingly an object of the invention to provide a cosmetic preparation for coloring the eyelids and eyebrows which overcomes the above-mentioned disadvantages of the prior art compositions of this general type, which does not run into folds and pockets in the skin.

The object is attained with an aqueous preparation that contains 0.1% by weight to 5% by weight of polyvinyl pyrrolidone, 4% by weight to 25% by weight of an alcohol from the group of ethanol and propanol, 2% by weight to 15% by weight of a dampening agent, 0.1% by weight to 5% by weight of polyoxyethylene glycerin fatty acid ester and/or polyether-modified polysiloxane, a colorant, and has a viscosity of less than 50 mPas (Brookfield, 25° C.). The viscosity was determined using a viscometer (Brookfield LV DV-III Ultra, rpm=20.0, spindle=CPE-40, shear rate=150 sec.$^{-1}$) at 20° C.

A preparation of this type can be applied to an eyelid or an eyebrow without difficulty using a capillary applicator, wherein the preparation is prevented from running in folds and pockets in the skin due primarily to the polyvinyl pyrrolidone. The preparation dries easily on the skin, without drawing excessive amounts of moisture out of it. On the other hand, the preparation exhibits only a slight tendency to dry out in the capillary application element of an applicator, which is achieved especially through a combination of one of the alcohols listed above with a humectant. The alcohol prevents the preparation from drying out during periods of non-use of the applicator. Any possible moisture extracting effect of the alcohol on the skin is compensated for by a humectant, which acts as a moisture contributor on the skin. In order to ensure sufficient viscosity levels to allow application with a capillary applicator, despite the viscosity-increasing substances contained in the preparation, especially the vinylpyrrolidone and, for example, also the pigments used as colorants, polyoxyethylene glycerin fatty acid ester or polyether-modified polysiloxane is added.

These substances counteract an increase in viscosity in the preparation, wherein a mixture of these substances is particularly effective. It was surprising that the preparation nevertheless exhibits a low tendency to run in folds and pockets in the skin, which is true to a particular degree with the addition of a mixture of these substances, wherein preferably concentration limits of 0.2% by weight to 5% by weight—referred to a single substance or a substance mixture—are used.

Depending upon the desired degrees of color, the ratio of colorant is 0.1% by weight to 15% by weight, wherein preferably color pigments are used. These generally produce stronger coloration as compared with soluble colorants. Application using a capillary system can be accomplished without difficulty, as long as a particle size of the pigments of D90% <10 μm is maintained. The water concentration in the preparation ranges from 35% by weight to 85% by weight.

Additives, such as skin care agents—like aloe vera, *Camilla sinensis*, tocopherol or pantenol—and preservatives are preferably limited to a maximum of 5% by weight.

Other features which are considered as characteristic for the invention are set forth in the appended claims.

Although the invention is described herein as embodied in a cosmetic preparation for coloring the eyelids and eyebrows, it is nevertheless not intended to be limited to the details described, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments.

DETAILED DESCRIPTION OF THE INVENTION

Example 1

Low-Viscosity Liquid for Coloring Eyebrows

| | |
|---|---|
| Demineralized water | 70.1% by weight |
| Ethanol | 20.0% by weight |
| Glycerin | 5.0% by weight |
| PVP K 15 [1] | 2.0% by weight |
| Polyether-modified polysiloxane [2] | 2.0% by weight |

-continued

| Colorant | |
|---|---|
| C.I. 16035 (red dye) | 0.6% by weight |
| C.I. 42090 (blue dye) | 0.1% by weight |
| C.I. 19140 (yellow dye) | 0.2% by weight |

A brown liquid for capillary systems with brush tips is obtained, with a viscosity of approximately 3.0 mPa s.

Example 2

| | |
|---|---|
| Deminerlized water | 68.4% by weight |
| 1.3 butanediol | 12.0% by weight |
| Ethanol | 8.0% by weight |
| PVP K 15 [1] | 3.0% by weight |
| Polyoxyethylene glycerin stearic acid ester[3] (CAS 68553-11-7) | 0.5% by weight |
| C.I. 42090 (blue dye) | 7.8% by weight |
| Camellia Sinensis Leaf Extract | 0.1% by weight |
| Methylparaben | 0.2% by weight |

The blue eyeliner solution that is obtained can be used in capillary applicators with flexible sintered tips, and has a viscosity of approximately 4 mPa s (25° C. Brookfield).

Example 3

Black Liquid for Coloring the Eyelids with Black Pigment

| | |
|---|---|
| Demineralized water | 65.0% by weight |
| Polyoxyethylene glycerin stearic acid ester[3] (CAS 68553-11-7) | 1.0% by weight |
| Polyether-modified polysiloxane [2] | 0.5% by weight |
| PVP K 30 [1] | 0.5% by weight |
| Propylene glycol | 10.0% by weight |
| Ethanol | 8.0% by weight |
| C.I. 77266 (inorganic black pigment) | 15.0% by weight |

Black eyeliner liquid having a viscosity of approximately 10 mPa s (Brookfield, 25° C.).

Additional information on the examples:

1) Available, for example, under the name PVP K 15 or PVP K 30 from the ISP firm, 50996 Cologne;

2) Available, for example, under the trade name Abil B8851 from the Goldschmidt firm, 45127 Essen;

3) Also known under the name PEG-30-glycerylstearate; available, for example, under the trade name Tagat S from the Goldschmidt firm, 45117 Essen;

The invention claimed is:

1. An aqueous cosmetic preparation for coloring eyelids and eyebrows, consisting of:
   0.1% by weight to 5% by weight of polyvinyl pyrrolidone;
   4% by weight to 25% by weight of an alcohol selected from the group consisting of ethanol and propanol;
   2% by weight to 15% by weight of a dampening agent;
   0.1% by weight to 5% by weight of a mixture consisting of a polyoxyethylene glycerin fatty acid ester and a polyether-modified polysiloxane;
   a maximum of 5% by weight of additives;
   a colorant; and
   the aqueous cosmetic preparation having a viscosity of less than 50 mPas, Brookfield at 25° C., said composition formulated as a preparation for coloring eyelids and eyebrows.

2. The preparation according to claim 1, wherein said colorant is 0.1% by weight to 15% by weight.

3. The preparation according to claim 2, wherein said colorant contains pigments having a particle distribution of D90% <10 μm.

\* \* \* \* \*